United States Patent [19]

Lazzara et al.

[11] Patent Number: 4,850,870
[45] Date of Patent: Jul. 25, 1989

[54] PROSTHODONTIC RESTORATION COMPONENTS

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 111,868

[22] Filed: Oct. 23, 1987

[51] Int. Cl.[4] .......................... A61C 8/00; A61C 13/30
[52] U.S. Cl. ...................................... 433/174; 433/173; 433/201.1
[58] Field of Search ....................... 433/173, 174, 201.1

[56] References Cited

U.S. PATENT DOCUMENTS

| 3,726,011 | 4/1973 | Savignano | 433/174 |
|---|---|---|---|
| 4,185,383 | 1/1980 | Heimke et al. | 433/173 |
| 4,215,986 | 8/1980 | Riess | 433/173 |
| 4,416,629 | 11/1983 | Mozsary et al. | 433/174 |
| 4,552,532 | 11/1985 | Mozsary | 433/173 |
| 4,722,688 | 2/1988 | Lonca | 433/173 |

FOREIGN PATENT DOCUMENTS

| 3531389 | 3/1987 | Fed. Rep. of Germany | 433/173 |
|---|---|---|---|
| WO85/2337 | 6/1985 | PCT Int'l Appl. | 433/174 |
| 2176709A | 1/1987 | United Kingdom | 433/174 |

Primary Examiner—Samuel Scott
Assistant Examiner—Allen J. Flanigan
Attorney, Agent, or Firm—Alfred H. Rosen

[57] ABSTRACT

Abutment posts and copings for use with dental implants are disclosed. The abutment post has at one end means to affix it to the implant so as to extend supragingivally from the implant through the gum tissue. The post tapers down in cross-section from a region at or near the exposed surface of the gum tissue to its free end, and has at its free end a socket for receiving the coping. The coping has at its open end a hollow flaring section dimensioned to fit over and envelop the tapered post section, and a socket section at the smaller end of the flaring section which fits over and mates with the socket on the post. The flaring section of the coping extends to the locus of the boundary between the post and the exposed surface of the gum tissue, where the coping and the post can meet along that locus and form a seal, or provide rigidity to the installed restoration.

15 Claims, 1 Drawing Sheet

U.S. Patent       Jul. 25, 1989       4,850,870
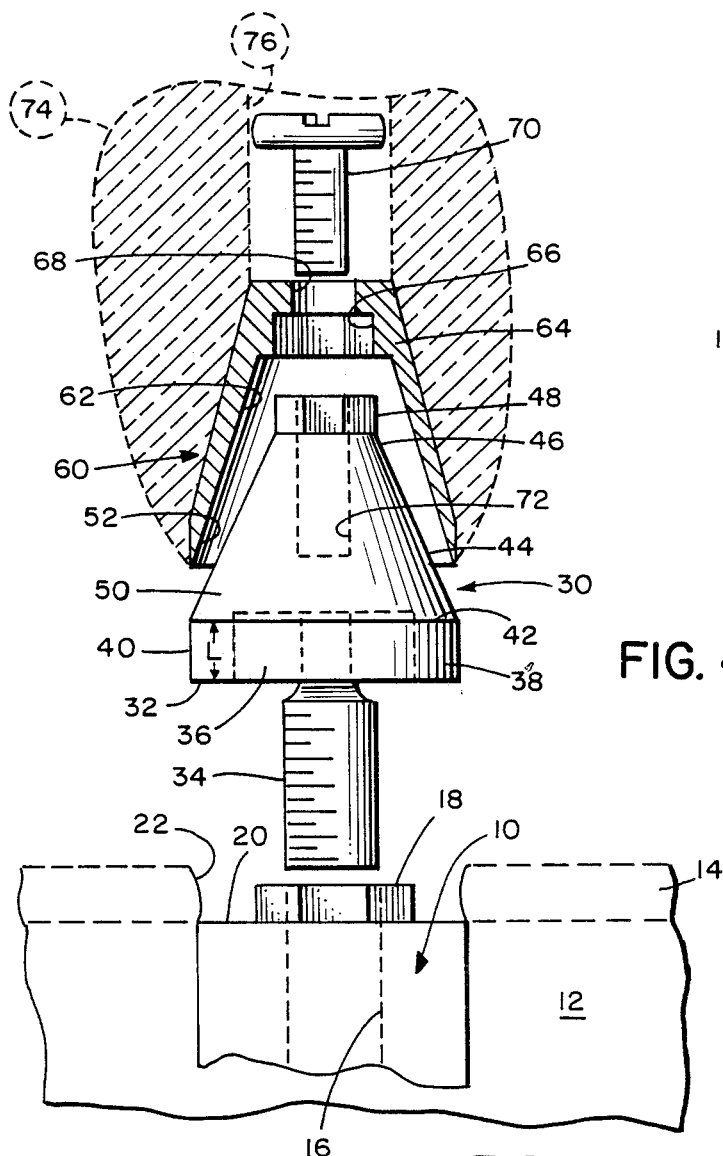
FIG. 1
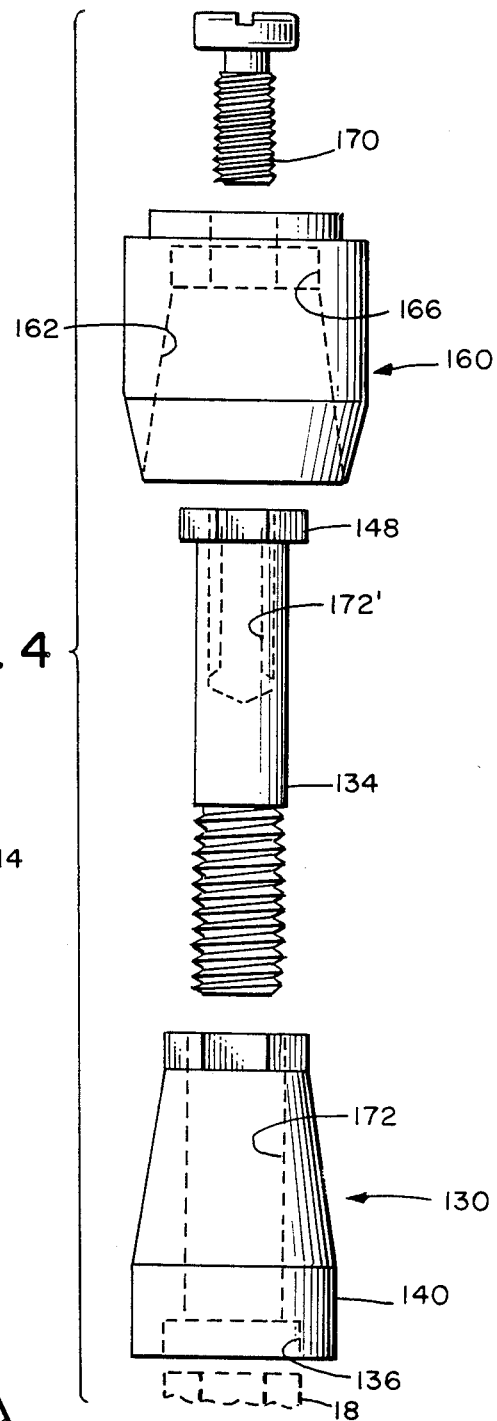
FIG. 4
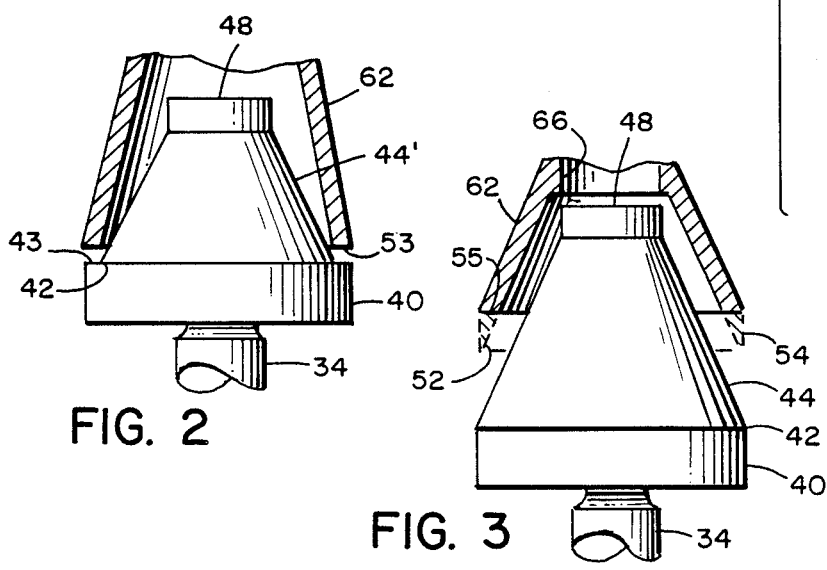
FIG. 2
FIG. 3

PROSTHODONTIC RESTORATION COMPONENTS

This invention relates in general to the field of prosthodontic restoration; more particularly to dental implant systems wherein an object substituting for a natural tooth root is surgically implanted in edentulous bone of the alveolar arches of the jaws, now commonly known as dental implants.

Dental implants are coming into increasingly-wide use, so much so that a new field of "implantology" is emerging, giving wider scope to the more general field of prosthodontic restoration. After one or more dental implants has or have been successfully implanted, usually by an oral surgeon, or a periodontist, in the jawbone(s) of a patient, the restorative dentist has the task of fashioning one or more prosthodontic restoration(s) and attaching it or them to the implants in a way that will provide a cosmetically attractive as well as structurally adequate dental restoration. Initial successes were based on structurally sound biocompatible implant devices realized in titanium which only recently became commercially available, and are now appearing in a variety of designs and configurations. Little or no attention was paid to cosmetic considerations, with the result that a restorative dentist seeking to provide a patient with an anatomically pleasing restoration must bring a considerable amount of personal ingenuity to the task of building the restoration, which is both expensive and time-consuming. A need exists to provide components which will enable a restorative dentist to link dental implants and prosthodontic restorations together into a structurally sound and cosmetically pleasing dental restoration. This invention addresses that need.

In a typical dental implant a titanium post is press-fitted or screwed into a hole drilled in a jawbone to receive it, and the post is left there, covered by the fleshy gum tissue until osseointegration takes place, firmly fixing the post in the jawbone. Thereafter, the gum tissue is opened to expose an end of the post, which may have a threaded or an unthreaded socket in it for the reception of a component or components intended to support a prosthodontic restoration or to facilitate the manufacture of such a restoration. The present invention provides an abutment post and a coping in a variety of materials for enabling a restorative dentist to make a prosthodontic restoration and to fix it in place on a component or components supported by the implant.

Generally according to the invention the abutment post has at one end means to affix it to the implant so as to extend supragingivally from the implant through the gum tissue. The post tapers down in cross-section from a region at or near the exposed surface of the gum tissue to its free end, and has at its free end a socket for receiving the coping. The coping has a hollow flaring section dimensioned to fit over and envelop the tapered post section, and a socket section at the smaller end of the flaring section which fits over and mates with the socket on the post. The flaring section of the coping extends to the locus of the boundary between the post and the exposed surface of the gum tissue, where the coping and the post can meet along that locus and form a seal, or provide rigidity to the installed restoration.

It is among the objects of the invention to provide such post-and-coping components in commercial quantities and materials for enabling restorative dentists to fashion cosmetically pleasing and structurally sound prosthodontic restorations with the same ease and reliability that has been heretofore available for cases involving only prepared natural dentitions and root-canal posts.

Another object of the invention is to provide such post-and-coping components in a design which lends itself to fabrication in a wide variety of sizes and shapes.

It is another object of the invention to provide such post-and-coping components which can incorporate anti-rotational features, useful for mounting and supporting a single-tooth restoration.

These and other objects and features of the invention will be explained with reference to certain exemplary embodiments of the invention that are illustrated in the accompanying drawings; in which:

FIG. 1 is an axially-exploded view of a post and coping, the coping being shown in section;

FIG. 2 is a partial view of a post and coping employing an alternative meeting mechanism between the flared end of the coping and the post at the locus near the surface of the gum tissue;

FIG. 3 is a partial view of another embodiment of the invention; and

FIG. 4 shows an embodiment of the invention intended for use in a single-tooth restoration.

In FIG. 1 an implant 10 is shown installed in a jawbone 12 covered with gum tissue 14. An internally-threaded bore 16 in the implant opens to the gum, where a hexagonal fitting 18 is provided at the top 20 of the implant. The implant 10 thus-far described is one of several that are now commercially available. Normal procedure with this kind of implant is to install the implant, close the bore 16 and allow the gum tissue to grow over it while osseointegration is permitted to take place. Later, preparatory to beginning prosthodontic restoration, the gum tissue is opened surgically to gain access to the implant. The present invention provides a means to preserve an opening 22 in the gum tissue during the preparation of a restoration.

An abutment post 30 according to the invention has at a first end 32 a screw 34 for engaging in the bore 16 and fixing the post to the implant. A re-entrant cavity 36 in the first end provides room to enclose the hexagonal fitting 18, and the screw extends out of this cavity from its bottom. A skirt 38 around the cavity has substantially the same outer diameter as the implant 10, and when the post 30 is affixed to the implant the annular surface of the post at its first end 32 mates with the surface of the top 20 of the implant 10. The outer cylindrical surface 40 of the skirt 38 has an axial length "L" which is substantially the same as the thickness of the gum tissue 14, providing a trans-tissue section of the post from which a tapered post section 50 extends supragingivally. In order to accomodate differences in gum thickness that exist in different parts of the mouth of an individual patient, as well as differences that will be encountered from one patient to another, posts 30 are provided in a variety of sizes among which the axial length "L" can be chosen to fit the need of a particular location in the mouth of a particular patient.

The supragingivally extending section 50 meets the transtissue section at a locus 42 between the cylindrical surface 40 and the tapering surface 44 of the supragingivally extending section, which latter tapers down to a smaller cross-section at its second end 46 more remote from the implant 10. A mount section 48 for a coping 60 (to be described) is fitted to the second end 46 of the post.

The coping 60 is a generally cone-shaped hollow body having a flaring section 62 dimensioned to fit over and envelop the supragingivally-extending post section 50, and at its narrower end 64 a socket section 66 dimensioned to fit over and snugly embrace the mount section 48. The socket section has a bore 68 through its top for the passage of a bolt 70. The supragingivally-extending post section 50 has an internally-threaded bore 72 extending through the mount section 48 for receiving the bolt 70. The coping 60 may be fastened to the post 30 with the bolt 70. The mount section 48 and the socket section 66 preferably have matching respective external and internal non-circular surface configurations (e.g: hexagonal, as shown), to prevent rotation of the coping around the post, when that feature is desired.

The flaring section 62 of the coping extends to an edge 52 which, as illustrated in FIG. 1, terminates in a circular locus which substantially matches and can mate with the locus 42 on the post 30 between the trans-tissue section and the supragingivally-extending section. When the bolt 70 is tightened the coping edge 52 may be brought snugly against the post at or near the locus 42, both to seal the space between the tapered sections of the post and the coping, and to provide a bearing remote from the bolt for mechanical stability between the two parts 30 and 60. The coping may flare at a smaller angle than the tape of the post, so that contact between the two parts is at the coping edge 52 and the socket section 66.

Ultimately a prosthodontic restoration, represented in dashedline as a tooth 74 is fashioned on the coping, or on a replica of the coping, depending on whatever restoration technique is used by the prosthodontist. To this end, the coping may be provided in a suitable metal or in a plastics material that can be consumed in a casting process, leaving the structural shape of the coping incorporated in the restoration. In the case where the coping is made of metal, and the tooth 74 is made of a frangible material such as porcelain fixed to it, tightening the bolt 70 should be done with care to avoid overstressing the coping at the flared edge 52. FIG. 2 illustrates a modification of the invention which may be better suited for use in that situation.

In FIG. 2 the tapered surface 44' of the supragingivally-extending section of the post terminates within the locus 42, to provide an annular shoulder 43 between the wide end of the tapered surface and the supragingival aspect of the cylindrical surface 40. This shoulder 43 lies substantially in a plane which is transverse to the direction in which the coping 60 is fitted over the post 30.

Correspondingly, the wider part of the flaring section 62 of the coping is terminated in a flat-annular surface 53, similarly oriented, which comes to rest on the shoulder 43 when the bolt 70 (not shown in FIG. 2) is tightened on the post. The components of force thereby created between the post and the coping are predominantly axial in direction, with little or no component of force in a radial direction.

FIG. 3 illustrates another way to remove the risk of marginal damage to a frangible restoration. In this embodiment the post is the same as in FIG. 1, but the flared section 62 of the coping is foreshortened to an annular end surface 55. The prosthodontist fashions a terminating portion 54 at this surface, including an edge 52, in a usual wax-up material. Then, when the restoration is made the flared section termination can be cast in the exact shape and size desired.

When two or more abutments are available on which to construct a restoration, there is no need to provide anti-rotation between the restoration and the abutments, or between the restoration components. In such a situation, the post, coping and implant may be free to rotate around a common axis relative to each other. On the other hand, when a single-tooth restoration is to be undertaken, the finished tooth should not be free to pivot on its abutment support. FIG. 4 illustrates an embodiment of the invention which incorporates anti-pivot, or anti-rotational features.

In FIG. 4 the post 130 has a socket 136 in its transtissue section 140 for anti-rotationally coupling with the fitting 18 of the implant. The post has a bore 172 extending axially entirely through it, and a first bolt 134 is used to fasten the post on the implant via the implant bore 16 (not shown in FIG. 4). The first bolt 134 has in turn a bore 172 extending from its supragingivally extending end part way into the first bolt, and at the supragingivally-extending end an anti-pivotal mount 148. The coping 160 has at its supragingivally-extending end, terminating the narrower end of the interior cone 162 a socket 166 for non-rotationally connecting the coping to the mount 148. A second bolt 170 is used to fix the coping 160 on the first bolt 134.

Referring by way of example to FIG. 1, when the bolt 70 is tightened, the hole 76 shown at the top of the tooth will be filled and sealed. Thereafter, access to the bolt can be had by drilling out the filling material. Restorations made using post-and-coping devices according to the invention can be disassembled for repair or replacement without risk of damage to underlying abutment supports.

We claim:

1. Prosthodontic restoration components for a dental implant system wherein an object substituting for a natural root is surgically implanted in edentulous bone of the alveolar arches of the jaws, said object providing, in the vicinity of the boundary between said bone and the fleshy gum tissue that covers said arches and normally invests the necks of natural teeth, receiving means for receiving and supporting such components, said components being an abutment post and a substantially rigid coping, said abutment post having at a first end means to affix said post to said receiving means so as to extend supragingivally from said implanted object through said gum tissue, said post having a trans-tissue section adjacent said first end, said trans-tissue section extending from said first end a distance substantially the same as the thickness of said gum tissue around said post, and a supragingivally-extending section which tapers in cross-section from said trans-tissue section to a smaller cross-section at its second end, and a mount section extending supragingivally from said second end on a substantially uniform cross-section for receiving said coping, said coping having a hollow flaring section open at its wide end and dimensioned to fit over and envelope said supragingivally-extending post section and a socket section at the smaller end of said flaring section dimensioned to fit snugly over said mount section, said flaring section extending at the boundary of its wide end to the locus of the boundary between said trans-tissue section and said supragingivally-extending section when said socket section is fitted over said mount section, and means engageable between said mount section and said socket section to bring said coping and said post into sealing contact between said respective boundaries.

2. Prosthodontic restoration components according to claim 1 wherein said boundary of said wider end of said flaring section has substantially the same shape and dimensions as said locus so that said wider end of said coping can closely contact said post at said locus when said coping is installed on said mount section.

3. Prosthodontic restoration components according to claim 1 including an artificial tooth affixed to said coping.

4. Prosthodontic restoration components according to claim 1 including a bolt for holding said socket affixed to said mount section, for affixing said coping to said post.

5. Prosthodontic restoration components according to claim 4 wherein said coping flares on a smaller angle than said tapered post, so that when said bolt is tightened the contact between the edge of said coping at the flared end and the post at said locus is tightened.

6. Prosthodontic restoration components according to claim 1 wherein said mount section and said socket section have substantially the same non-circular cross-section.

7. Prosthodontic restoration components according to claim 6 including means to prevent rotation of said post on said receiving means.

8. Prosthodontic restoration components according to claim 7 wherein said abutment post has a threaded bolt extending through said post into said implanted object for clamping said post to said implanted object over said receiving means, and a recess in said first end of said abutment post, said receiving means including a projecting part fitting into said recess, said projecting part and said recess having substantially identical non-circular transverse profiles of substantially the same size.

9. Prosthodontic restoration components according to claim 8 including a second threaded bolt for holding said socket affixed to said mount section, for affixing said coping to said post, said first-named threaded bolt having in the end remote from said implanted object a threaded socket for receiving said second threaded bolt.

10. Prosthodontic restoration components according to claim 2 wherein said supragingivally-extending section of said post has the same cross-sectional dimensions as said transtissue section at said locus.

11. Prosthodontic restoration components according to claim 2 wherein said supragingivally-extending section of said post has smaller cross-sectional dimensions than said trans-tissue section at said locus, providing a substantially annular shoulder extending transversely between said sections, and said flaring section of said copying terminates at said wider end in a substantially flat annular boundary surface for contacting said shoulder in a plane that is transverse to the direction in which said coping is fitted over said post.

12. Prosthodontic restoration components according to claim 1 wherein said flaring section of said coping is foreshortened, and an after-fitted terminal member is fitted to said section to provide said boundary of said wider end.

13. Prosthodontic restoration components according to claim 1 in which said coping makes contact with said post substantially only at said mount section and said locus.

14. Prosthodontic restoration components for a dental implant system wherein an object substituting for a natural root is surgically implanted in edentulous bone of the alveolar arches of the jaws, said object providing, in the vicinity of the boundary between said bone and the fleshy gum tissue that covers said arches and normally invests the necks of natural teeth, receiving means for receiving and supporting such components, said components being an abutment post and a substantially rigid coping, said abutment post having at a first end means to affix said post to said receiving means so as to extend supragingivally from said implanted object through said gum tissue, said post having a trans-tissue section adjacent said first end, said trans-tissue section extending from said first end a distance substantially the same as the thickness of said gum tissue around said post, and a supragingivally-extending section which tapers in cross-section from said trans-tissue section to a smaller cross-section at its second end, and a mount section of substantially uniform cross-section at said second end for receiving said coping, said coping having a hollow flaring section open at its wide end and dimensioned to fit loosely over and envelop said supragingivally-extending post section and a connecting section at the smaller end of said flaring section dimensioned to interfit snugly with said mount section, said flaring section extending at the boundary of its wide end to the locus of the boundary between said trans-tissue section and said supragingivally-extending section when said connecting section is interfitted with mount section, and means engageable between said mount section and said connecting section to bring said coping and said post into sealing contact between said respective boundaries.

15. Prosthodontic restoration components according to claim 14 in which said coping makes contact with said post subtantially only at said mount section and said locus.

* * * * *

(12) REEXAMINATION CERTIFICATE (4400th)
United States Patent
Lazzara et al.

(10) Number: US 4,850,870 C1
(45) Certificate Issued: Jul. 24, 2001

(54) PROSTHODONTIC RESTORATION COMPONENTS

(75) Inventors: Richard J. Lazzara, Lake Worth; Keith D. Beaty, West Palm Beach, both of FL (US)

(73) Assignee: Implant Innovations, Inc., West Palm Beach, FL (US)

Reexamination Request:
No. 90/005,703, Apr. 14, 2000

Reexamination Certificate for:
Patent No.: 4,850,870
Issued: Jul. 25, 1989
Appl. No.: 07/111,868
Filed: Oct. 23, 1987

(51) Int. Cl.[7] .............................. A61C 8/00; A61C 13/30
(52) U.S. Cl. ........................ 433/174; 433/173; 433/201.1
(58) Field of Search .................................. 433/172, 173, 433/174, 175, 176, 201.1

(56) References Cited

U.S. PATENT DOCUMENTS

| | | | | |
|---|---|---|---|---|
| 3,726,011 | * | 4/1973 | Savignano | 433/174 |
| 3,732,621 | | 5/1973 | Bostrom | 32/10 A |
| 4,185,383 | * | 1/1980 | Heimke et al. | 433/173 |
| 4,215,986 | * | 8/1980 | Riess | 433/173 |
| 4,416,629 | * | 11/1983 | Mozsary et al. | 433/174 |
| 4,552,532 | * | 11/1985 | Mozsary | 433/173 |
| 4,722,688 | * | 2/1988 | Lonca | 433/173 |
| 4,854,872 | | 8/1989 | Detsch | 433/173 |

FOREIGN PATENT DOCUMENTS

| | | | | |
|---|---|---|---|---|
| 3531389 | * | 3/1987 | (DE) | 433/173 |
| 2176709 | * | 1/1987 | (GB) | 433/174 |
| WO85/2337 | * | 6/1985 | (WO) | 433/174 |

OTHER PUBLICATIONS

Brånemark, et al., "*Osseointegrated Implants In The Treatment Of The Edentulous Jaw,*" Almqvist & Wiksell International, 1977, pp. Front cover, 1–132 back cover.
Calcitek, Inc., "*Biointegration: Integral—The Natural Step Forward in Dental Implants,*" Jan. 1987, 4 pages.
Calcitek, Inc., "*Integral: Biointegrated Dental Implant System Coated with Calcitite Brand Hydroxylapatite—Price List and Ordering Information,*" Sep. 1987, 9 pages.

* cited by examiner

*Primary Examiner*—John J. Wilson

(57) ABSTRACT

Abutment posts and copings for use with dental implants are disclosed. The abutment post has at one end means to affix it to the implant so as to extend supragingivally from the implant through the gum tissue. The post tapers down in cross-section from a region at or near the exposed surface of the gum tissue to its free end, and has at its free end a socket for receiving the coping. The coping has at its open end a hollow flaring section dimensioned to fit over and envelop the tapered post section, and a socket section at the smaller end of the flaring section which fits over and mates with the socket on the post. The flaring section of the coping extends to the locus of the boundary between the post and the exposed surface of the gum tissue, where the coping and the post can meet along that locus and form a seal, or provide rigidity to the installed restoration.

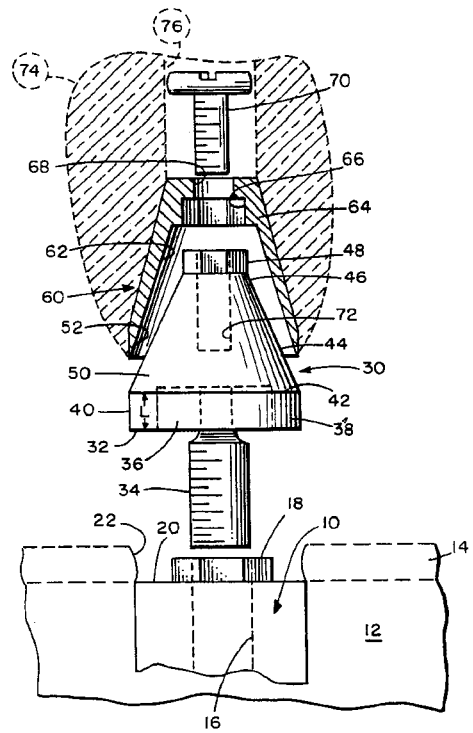

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

\* \* \* \* \*